(12) United States Patent
Wolters et al.

(10) Patent No.: US 7,787,114 B2
(45) Date of Patent: Aug. 31, 2010

(54) SYSTEMS AND METHODS FOR INSPECTING A SPECIMEN WITH LIGHT AT VARYING POWER LEVELS

(75) Inventors: Christian Wolters, Campbell, CA (US); Jon Meyer, Fremont, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 109 days.

(21) Appl. No.: 11/759,092

(22) Filed: Jun. 6, 2007

(65) Prior Publication Data

US 2008/0304069 A1    Dec. 11, 2008

(51) Int. Cl.
*G01N 21/00* (2006.01)

(52) U.S. Cl. .............. 356/237.2; 250/214.1; 250/205; 250/492.1; 356/237.1; 356/445; 356/446

(58) Field of Classification Search ............ 250/214, 250/214.1, 205, 207, 492.1; 356/237.1–237.5, 356/236, 445, 446
See application file for complete search history.

(56) References Cited

U.S. PATENT DOCUMENTS

| | | | |
|---|---|---|---|
| 5,361,268 A * | 11/1994 | Fossey et al. .............. 372/23 |
| 6,002,122 A | 12/1999 | Wolf |
| 6,201,601 B1 | 3/2001 | Vaez-Iravani et al. |
| 6,271,916 B1 | 8/2001 | Marxer et al. |
| 6,538,730 B2 | 3/2003 | Vaez-Iravani et al. |
| 6,833,913 B1 * | 12/2004 | Wolf et al. ............... 356/237.2 |
| 7,057,135 B2 * | 6/2006 | Li ........................ 219/121.7 |
| 7,130,036 B1 | 10/2006 | Kuhlmann et al. |
| 7,424,192 B2 * | 9/2008 | Hochberg et al. ........... 385/122 |
| 7,436,508 B2 * | 10/2008 | Wolters et al. ........... 356/237.5 |
| 2003/0058433 A1 | 3/2003 | Almogy et al. |
| 2006/0274304 A1 | 12/2006 | Haller et al. |
| 2006/0285112 A1 | 12/2006 | Reich et al. |
| 2007/0012867 A1 | 1/2007 | Wolters et al. |
| 2007/0013898 A1 | 1/2007 | Wolters et al. |
| 2007/0013899 A1 | 1/2007 | Wolters et al. |
| 2007/0081151 A1 | 4/2007 | Shortt et al. |

OTHER PUBLICATIONS

U.S. Appl. No. 10/719,347, filed Nov. 21, 2003, Shortt et al.
U.S. Appl. No. 11/110,383, filed Apr. 20, 2005, Shortt et al.
U.S. Appl. No. 60/772,418, filed Feb. 9, 2006, Kirk et al.
International Search Report and Written Opinion for PCT/US2008/066124 mailed on Sep. 1, 2008.

* cited by examiner

*Primary Examiner*—Gregory J Toatley, Jr.
*Assistant Examiner*—Iyabo S Alli
(74) *Attorney, Agent, or Firm*—Ann Marie Mewherter

(57) ABSTRACT

Systems and methods for inspecting a specimen with light at varying power levels are provided. One system configured to inspect a specimen includes a light source configured to generate light. The system also includes a power attenuator subsystem configured to alter a power level of the light directed to the specimen during inspection between at least two power levels including a full power level and a minimum power level equal to or greater than about 10% of the full power level. In addition, the system includes a detection subsystem configured to generate output responsive to the light scattered from the specimen. The output can be used to detect defects on the specimen.

15 Claims, 6 Drawing Sheets

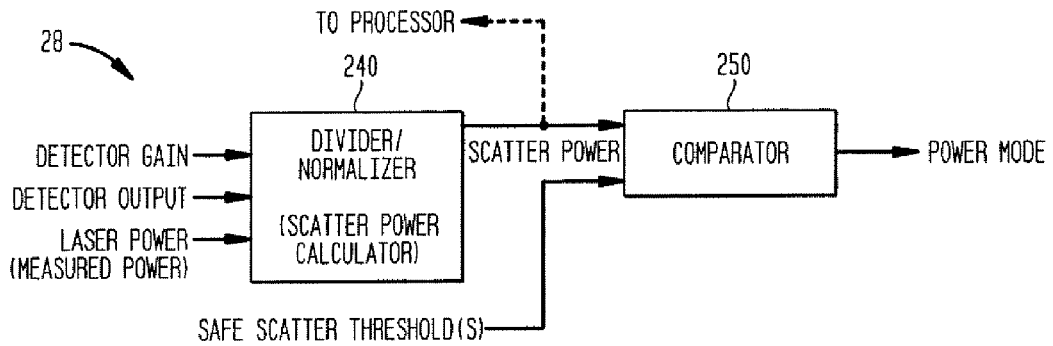
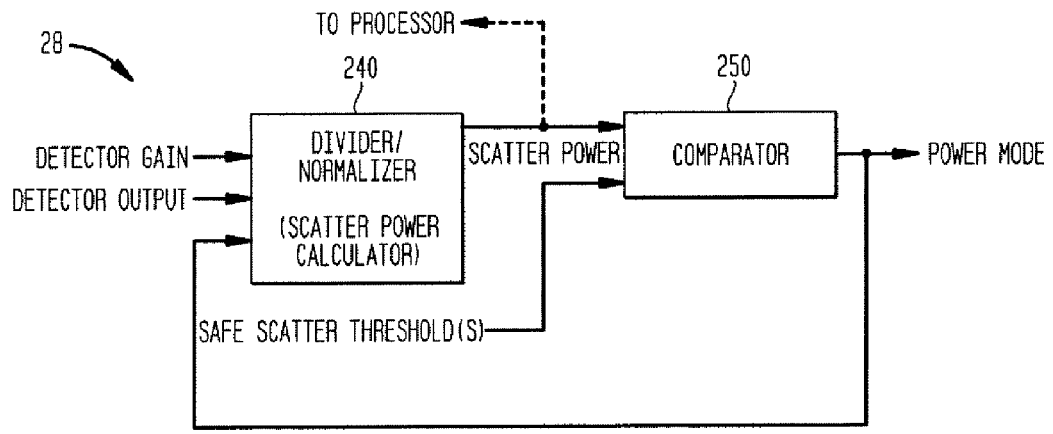
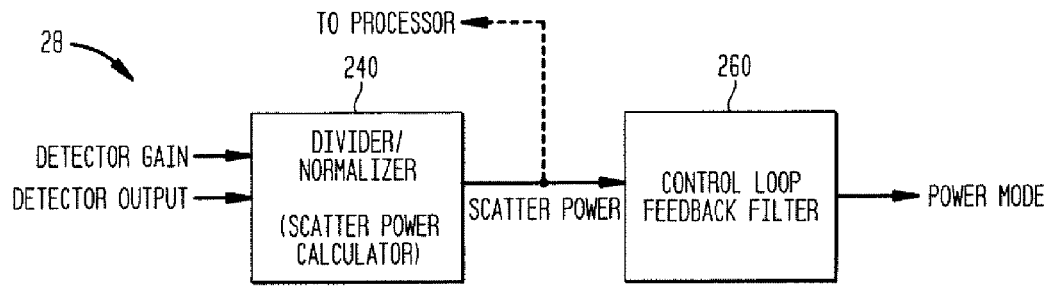

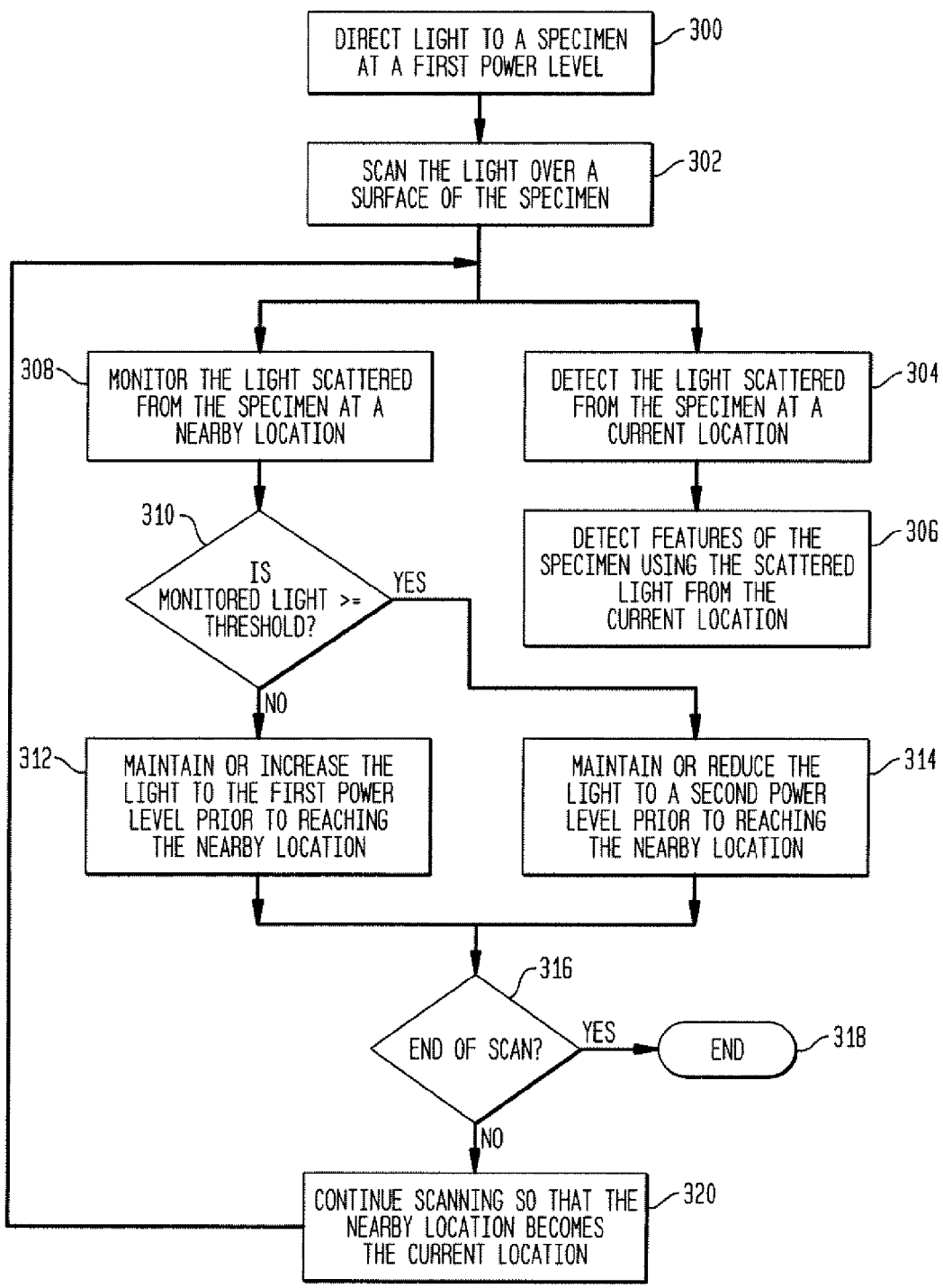

SYSTEMS AND METHODS FOR INSPECTING A SPECIMEN WITH LIGHT AT VARYING POWER LEVELS

BACKGROUND OF THE INVENTION

1. Field of the Invention

The present invention generally relates to systems and methods for inspecting a specimen with light at varying power levels. Certain embodiments relate to a system configured to inspect a specimen that includes a power attenuator subsystem configured to alter a power level of light directed to the specimen during inspection 2. Description of the Related Art The following description and examples are not admitted to be prior art by virtue of their inclusion in this section.

Fabricating semiconductor devices, such as logic, memory and other integrated circuit devices, typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process, and thus, higher profits. Inspection has always been an important part of semiconductor fabrication. However, as the dimensions of semiconductor devices decrease, inspection becomes even more important to the successful manufacture of acceptable semiconductor devices. For instance, detecting defects of decreasing size has become increasingly necessary, since even relatively small defects may cause unwanted aberrations in the semiconductor device, and in some cases, may cause the device to fail.

Many different types of inspection tools have been developed for the inspection of semiconductor wafers, including optical and E-beam systems. Optical inspection tools may be generally characterized into dark-field and bright-field inspection systems. Dark-field systems are typically known for having a relatively high detection range. For instance, dark-field systems detect the amount of light that is scattered from the surface of a specimen when an incident beam is directed to the specimen at a normal or oblique angle. The amount of scattered light detected by the system generally depends on the optical characteristics of the spot under inspection (e.g., the refractive index of the spot), as well as any spatial variations within the spot (e.g., uneven surface topologies). In the case of dark-field inspection, smooth surfaces lead to almost no signal, while surfaces with protruding features (such as patterned features or defects) tend to scatter much more strongly (sometimes up to six orders of magnitude or more). Bright-field inspection systems direct light to a specimen at a particular angle and measure the amount of light reflected from the surface of the specimen at a similar angle. In contrast to dark-field systems, the variations in the reflected signal collected by a bright-field system are generally no more than about two orders of magnitude.

In addition, most inspection tools are designed to inspect either unpatterned or patterned semiconductor wafers, but not both. Since the tools are optimized for inspecting a particular type of wafer, they are generally not capable of inspecting different types of wafers for a number of reasons. For example, many unpatterned wafer inspection tools are configured such that all of the light collected by a lens (or another collector) is directed to a single detector that generates a single output signal representative of all of the light collected by the lens. Therefore, light scattered from patterns or features on a patterned wafer will be combined with other scattered light (e.g., from defects). In some cases, the single detector may become saturated, and as a result, may not yield signals that can be analyzed for defect detection. Even if the single detector does not become saturated, the light scattered from patterns or other features on the wafer cannot be separated from other scattered light thereby hindering, if not preventing, defect detection based on the other scattered light.

Tools used for inspecting patterned wafers generally employ at least two detectors for improved spatial resolution. However, the detectors used in patterned wafer inspection tools may also become saturated, especially when imaging with a dark-field system. As noted above, dark-field scattering signals obtained from a patterned wafer may vary by six orders of magnitude (or more) due to the variation in surface topology from smooth surface regions (which appear dark) to highly textured regions (which appear bright). It is often difficult, especially with detection systems operating at high data rates, to collect meaningful signals from both the dark and the bright areas of the substrate being inspected without "on-the-fly" adjustment.

Most optical inspection tools are limited in either detection range, detection sensitivity, or both. For example, inspection tools employing high-gain detectors to obtain higher detection range may be incapable of detecting smaller (i.e., low light) signals. On the other hand, inspection tools with lower gain detectors may achieve greater sensitivity at the cost of reduced detection range. In other words, although lower gain detectors may be capable of detecting smaller signals, they may become saturated when larger signals are received. Other factors tend to limit the detection range, in addition to detector gain. For example, further limitations may be imposed by the amplification circuitry or the fast analog-to-digital converters used to convert the scattered output signals into a format suitable for signal processing.

One possible solution to this problem is to apply non-linear amplification to the output signal of a detector in order to emphasize the low-amplitude signal range. An approach of this sort is described by Wolf in U.S. Pat. No. 6,002,122, which is incorporated by reference as if fully set forth herein. In the method described by Wolf, the output signal from a photomultiplier tube (PMT) is processed by a logarithmic amplifier and gain correction mechanism. Wolf emphasizes the low-amplitude signal range by changing the PMT gain "on-the-fly" (by changing the bias potentials supplied to the dynodes) to avoid anode saturation, a common detection range limitation of PMT detectors. Although this approach may provide improved visibility of small-signal defects in the dark-field image, it does nothing to extend the overall detection range of the inspection system. In addition, the "on-the-fly" gain modulation disclosed by Wolf causes the PMT to be operated in a highly non-linear way, thus requiring complex (and expensive) drive electronics and sophisticated calibrations to compensate for the non-linear and transient effects.

Another approach to extend the detection range of an inspection system is to utilize two or more detectors with separate detection channels. An approach of this sort is described by Almogy et al. in U.S. patent application Ser. No. 2003/0058433, which is incorporated by reference as if fully set forth herein. Almogy describes a defect detection system that utilizes at least two detectors. One of the detectors is optimized for high sensitivity, while the other is designed to have a high saturation level, typically at the expense of sensitivity. The light scattered from a specimen is split among the detectors with the addition of various optical components. Though Almogy is able to extend the detection range, Almogy does so by requiring multiple detectors with additional optics and electronic circuitry, all of which consume additional space, increase complexity, and incur higher cost.

Therefore, a need remains for improved systems and methods for extending the detection range of a wafer inspection system. Preferably, such improved systems and methods would provide significant measurement range extension without the complexity and cost of real-time gain adjustment, as required by Wolf, or the additional detectors, optics, and electronic circuitry required by Almogy. In addition, an improved inspection system would extend the detection range without sacrificing throughput or sensitivity. In some cases, the improved inspection system may be used for inspecting both patterned and unpatterned wafers.

SUMMARY OF THE INVENTION

The following description of various embodiments of systems and methods is not to be construed in any way as limiting the subject matter of the appended claims.

One embodiment relates to a system configured to inspect a specimen. The system includes a light source configured to generate light. The system also includes a power attenuator subsystem configured to alter a power level of the light directed to the specimen during inspection between at least two power levels including a full power level and a minimum power level equal to or greater than about 10% of the full power level. In addition, the system includes a detection subsystem configured to generate output responsive to light scattered from the specimen. The output can be used to detect defects on the specimen.

In one embodiment, the power attenuator subsystem is configured such that a stability of the minimum power level is greater than a stability of a full extinction power level. In another embodiment, the power attenuator subsystem is configured such that the minimum power level is substantially insensitive to changes in alignment of the light source. In an additional embodiment, the power attenuator subsystem is configured such that the minimum power level is substantially insensitive to changes in a voltage applied to one or more elements of the power attenuator subsystem.

In one embodiment, the power attenuator subsystem is configured to alter the power level by altering a position of a wave plate. In another embodiment, the power attenuator subsystem includes a wave plate having a phase retardation selected such that the minimum power level achievable by the power attenuator subsystem is equal to or greater than about 10% of the full power level. In an additional embodiment, the power attenuator subsystem includes a wave plate having a phase retardation other than about half-wave retardation. In a further embodiment, the power attenuator subsystem includes a wave plate having a phase retardation of about wavelength/2.5 retardation.

In some embodiments, the power attenuator subsystem is configured to alter the power level by altering a voltage applied to a Pockel's Cell. In one embodiment, the power attenuator subsystem includes a Pockel's Cell oriented such that the minimum power level achievable by the power attenuator subsystem is equal to or greater than about 10% of the full power level. In another embodiment, the power attenuator subsystem includes a Pockel's Cell oriented at an angle other than about 0 degrees or about 45 degrees from a full extinction position of the Pockel's Cell. In an additional embodiment, the power attenuator subsystem includes a Pockel's Cell oriented at an angle of about 5 degrees to about 40 degrees from a full extinction position of the Pockel's Cell. In a further embodiment, the power attenuator subsystem includes a Pockel's Cell oriented at an angle of about 18.5 degrees from a full extinction position of the Pockel's Cell.

In one embodiment, the power attenuator subsystem is configured to alter the power level dynamically based on the output. In another embodiment, the minimum power level is below an incident power density associated with the onset of thermal damage of a feature of predetermined size on the specimen. In one such embodiment, the minimum power level is above an incident power density associated with a minimum of the scattered light that must be detected by the detection subsystem to generate the output that can be used to detect defects on the specimen. In an additional embodiment, the power attenuator subsystem is configured to alter the power level to the full power level during the inspection of features smaller than a predetermined size on the specimen. In some embodiments, the light source has an output power density of about 1 kW/cm$^2$ to about 1000 kW/cm$^2$. Each of the embodiments of the system described above may be further configured as described herein.

Another embodiment relates to a system configured to provide illumination of a specimen for inspection. The system includes a power attenuator subsystem configured to alter a power level of light directed to the specimen during the inspection between at least two power levels including a full power level and a minimum power level equal to or greater than about 10% of the full power level. This embodiment may be further configured as described herein.

An additional embodiment relates to a method for inspecting a specimen. The method includes altering a power level of light directed to the specimen during inspection between at least two power levels including a full power level and a minimum power level equal to or greater than about 10% of the fall power level. The method also includes generating output responsive to light scattered from the specimen. The output can be used to detect defects on the specimen. The method may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIGS. 9-11 are block diagrams of exemplary embodiments of a power controller subsystem, which may be included in the system of FIG. 1; and FIG. 12 is a flow chart diagram of a method for dynamically altering the amount of incident power directed to a specimen during inspection, so as to reduce thermal damage of features of predetermined size on the specimen and extend the measurement detection range of the system of FIG. 1.

Figure 1:
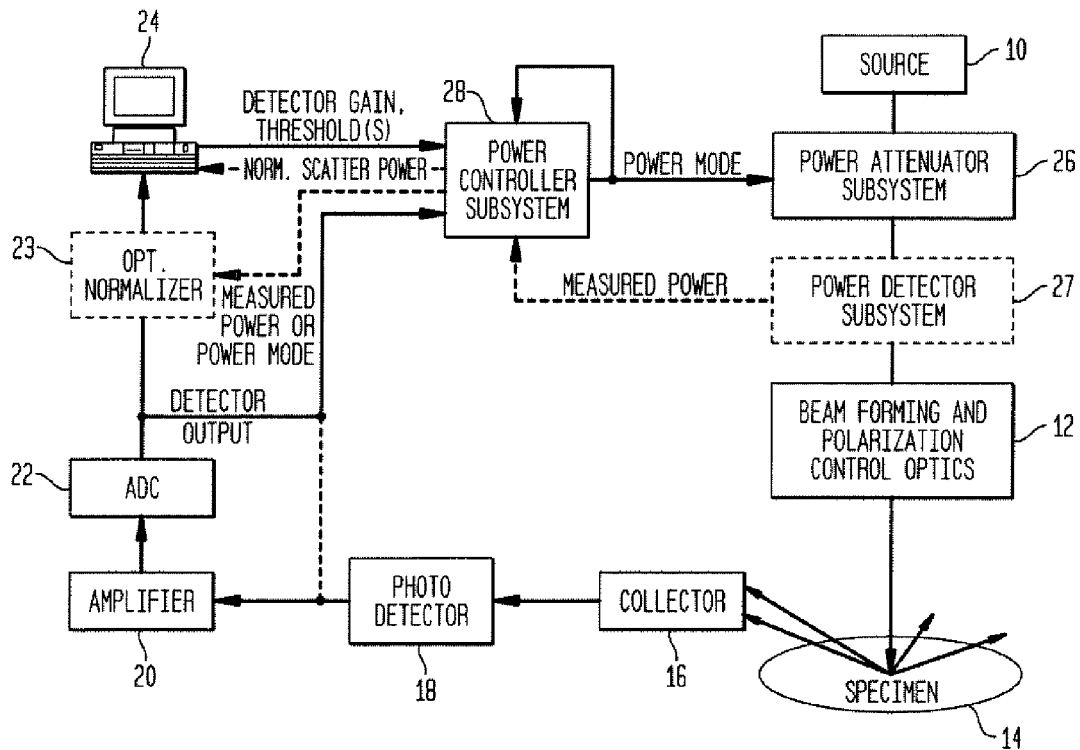
FIG. 1 is a block diagram illustrating one embodiment of a system configured to inspect a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle, a wafer, or any other sample known in the art that may be inspected for defects, features, or other information (e.g., an amount of haze or film properties). The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to a substrate formed of a semiconductor or non-semiconductor material. Examples of such a semiconductor or non-semiconductor material include, but are not limited to, monocrystalline silicon, is gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

The figures described herein generally illustrate exemplary circuits, systems, and methods that can be used for reducing particle damage during surface inspection scans, which use high-power light-based inspection systems, by dynamically reducing the incident power before scanning over large, highly scattering particles. Though relatively few embodiments are shown, one skilled in the art will readily understand how the various concepts described herein could be applied to produce alternative embodiments with similar functionality.

In high-power light-based inspection systems, the power density of the incident beam typically ranges between about 1 $kW/cm^2$ to about 1000 $kW/cm^2$. Unfortunately, particle damage often occurs during surface inspection scans with high power density light beams, due to the rapid power transfer from the light beam to a particle (or a portion of a particle) on the specimen. Particles not capable of dissipating large amounts of power tend to warm up quickly, and often explode due to insufficient power dissipation. For example, organic materials (such as photoresist particles) tend to dissipate significantly less power than inorganic materials (such as metallic particles), and therefore, tend to experience more damage. Unfortunately, exploded particles lead to debris, which can spread contamination over a large area of the specimen.

Methods that may be used to reduce thermal damage include methods for scanning the entire wafer at a reduced power (e.g., a factor of 10 less power) or an increased spot size (e.g., 2.5× to 5.7× larger spot size) than the power or spot size known to inflict damage. Another method may exclude the wafer center from inspection by blocking a portion of the incident beam. This method reduces thermal damage by eliminating the high power level typically supplied to the center region of the wafer. However, these methods either reduce sensitivity by reducing the signal-to-noise ratio (i.e., when reducing the power or increasing the spot size), or result in incomplete inspection of the wafer (i.e., when excluding the center). As such, the above-mentioned methods often miss defects on the wafer, due to poor sensitivity or outright exclusion.

On the contrary, the embodiments described herein are based on the observation that larger particles (typically greater than about 5 μm) are more likely to be damaged by the incident beam than smaller particles. For example, larger particles have more surface area, and as such, tend to absorb significantly more power than smaller particles having less surface area. Larger particles also tend to scatter significantly more light than smaller particles, due to larger surface area and/or increased surface irregularities. For example, the amount of light scattered from a particle of radius, R, is relatively proportional to the particle radius raised to the sixth power (i.e., $R^6$).

The embodiments described herein exploit the highly scattering properties of large particles to reduce thermal damage during a surface inspection scan. As set forth in more detail below, thermal damage may be avoided by detecting the presence of a large particle and reducing the incident beam power before a main portion of the beam reaches the large particle. In one embodiment, the power reduction may be provided by a relatively fast power attenuator subsystem, which can be configured to reduce the incident power to "safe" levels when scanning over large particles. The power attenuator subsystem can be configured to maintain (or increase) the incident power at "full" power when scanning lower-scatter portions of the wafer.

The embodiments described herein also provide methods and systems that allow optical adjustment of light power (e.g., laser power) between at least two pre-defined power levels with relatively high accuracy and stability, particularly compared to other methods and systems for altering the light power. In particular, the embodiments described herein address the power stability issues for power levels near extinction. For instance, one system that can be used to alter the light power includes a rotating half-wave (λ/2) plate and a polarizing beam splitter. With the half-wave plate in the nominal position, the polarization of the light is not changed, and the beam splitter transmits all of the light. When the half-wave plate is rotated by an angle, ϕ, the polarization of the light is rotated by twice that angle resulting in a transmission through the beam splitter of $I=I_0*(\cos(2*\phi))^2$.

This system has a number of disadvantages including that the power stability is limited when power levels are near full extinction (i.e., near 0% transmission). In particular, the relative intensity variation for small angle changes goes to infinity near full extinction: $(dI/I)/d\ \phi=-4\tan(2\phi)$. This variation approaches infinity when ϕ reaches 45 degrees. (Of course in real world applications, the imperfections of the optical components will somewhat reduce this effect, so infinity will never actually be reached.) Therefore, if a system includes a λ/2 plate-beam splitter configuration for power attenuation, the light attenuation value will be difficult to adjust to the selected level (e.g., about 10% transmission) and will be sensitive to changes in the alignment of the light source (e.g., after light source replacement).

Another system that can be used to alter the light power includes a Pockel's Cell and a beam splitter. A Pockel's Cell acts like a tunable wave plate in the beam path with phase shift from 0 to λ/2 controlled by a high voltage (HV) applied to the cell. The intensity, after the beam splitter is a function of phase shift θ, becomes: $I=I_0*(\cos(\theta/2))^2$. Such a system has disadvantages similar to those of the other systems described above. In particular, the relative intensity variation for small angle changes goes to infinity near full extinction: $(dI/I)/d\ \phi=-\tan(\theta/2)\to$infinity, $\theta\to 180$ degrees. As such, if a system uses a Pocket's Cell to attenuate the light power substantially rapidly, the correct setpoint for the drive HV that determines the phase retardation is limited to a narrow window. Any drift in the HV supply or other instability (e.g., ringing during the on/off phase) will appear magnified.

An additional system that can be used to alter the light power includes an actuated optical density (OD) filter moved into and out of the light path. However, this system is disadvantageous since moving an optical element into and out of the light path typically results in unfavorable beam deviation. OD filters are also known to degrade after prolonged use in ultraviolet (UV) applications.

FIG. 1 illustrates one embodiment of a system configured to inspect a specimen. In particular, FIG. 1 illustrates one embodiment of a system that may be used to reduce and/or prevent thermal damage to a specimen during a surface inspection scan. Thermal damage to a specimen is commonly caused by currently used systems when the incident light directed to the specimen is absorbed and inadequately dissipated by a feature on the specimen (such as large particles or defects). In addition to preventing thermal damage, the system of FIG. 1 can be used to provide an extended measurement detection range.

The system shown in FIG. 1 includes a dark-field optical subsystem. The illustrated system may be altered in many ways while still providing the capability to perform the methods described herein. In addition, the illustrated system may include various additional components that are not shown in FIG. 1 such as a stage, a specimen handler, folding mirrors, polarizers, additional light sources, additional collectors, etc. All such variations are within the scope of the embodiments described herein.

Furthermore, it is noted that FIG. 1 is provided herein to generally illustrate one embodiment of a configuration for a system configured to inspect a specimen. Obviously, the system configuration described herein may be altered to optimize the performance of the system as is normally performed when designing a commercial inspection system. In addition, the systems described herein may be implemented using an existing inspection system (e.g., by adding the power attenuator subsystem described herein to an existing inspection system). Examples of such existing inspection systems that may be modified to include a power attenuation subsystem described herein are illustrated in U.S. Pat. No. 6,201,601 to Vaez-Iravani et al., U.S. Pat. No. 6,271,916 to Marxer et al., and U.S. Pat. No. 6,538,730 to Vaez-Iravani et al., and commonly assigned, copending U.S. patent application Ser. No. 10/663,603 filed Sep. 16, 2003 by Kuhlmann et al., Ser. No. 10/719,347 filed Nov. 21, 2003 by Shortt et al., Ser. No. 11/110,383 filed Apr. 20, 2005 by Shortt et al., Ser. No. 11/145,874 filed Jun. 6, 2005 by Haller et al., Ser. No. 11/155,026 filed Jun. 16, 2005 by Reich et al., Ser. No. 11/244,451 filed Oct. 6, 2005 by Shortt et al., and 60/772,418 filed Feb. 9, 2006 by Kirk et al., which are incorporated by reference as if fully set forth herein. The embodiments described herein may be further configured as described in these patents and patent applications. For some such systems, the power attenuation capability described herein may be provided as optional functionality of the system (e.g., in addition to other pre-existing functionality of the system). Alternatively, the system described herein may be designed "from scratch" to provide a completely new system.

The system illustrated in FIG. 1 includes light source 10 configured to generate light. In one embodiment, the light source has an output power density of about 1 kW/cm$^2$ to about 1000 kW/cm$^2$. Therefore, the system shown in FIG. 1 may be a high-power optical inspection system. Light source 10 may include any number of light sources having output power densities ranging from about 1 kW/cm$^2$ to about 1000 kW/cm$^2$. Examples of high-power, laser-based sources that may be used for light source 10 include, but are not limited to, a diode laser, a solid state laser, a diode pumped solid state (DPSS) laser, and various gas lasers (such as a helium neon laser, an argon laser, etc.). In some cases, light source 10 may be a high-power, non-laser-based source, such as an Arc lamp, a Mercury high or low pressure lamp, an LED array, a light bulb, etc.

The light source may be configured to emit near monochromatic light or broadband light. In general, the system is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the system may also include one or more spectral filters that may limit the wavelength of the light directed to the specimen. The one or more spectral filters may be bandpass filters and/or edge filters and/or notch filters. In addition, the light generated by light source 10 may include UV light and/or any other suitable light known in the art.

The system also includes beam forming and polarization control optics 12. The beam of light generated by light source 10 (i.e., the "generated light") is directed to a surface of specimen 14 through beam forming and polarization control optics 12. To eliminate confusion, the light that reaches the surface of the specimen will be referred to herein as the "incident light" or the "incident laser beam." As described in more detail below, the "incident light" may differ from the "generated light" in one or more ways, including polarization, intensity, size and shape of the spot, etc.

The beam forming and polarization control optics may include optics for directing and supplying an incident beam to specimen 14 with, e.g., a particular spot size If the light source is configured to emit light of various polarizations, the system may also include one or more polarizing components that may alter the polarization characteristics of the light emitted by the light source. In some cases, the light directed to specimen 14 may be coherent or incoherent. Beam forming and polarization control optics 12 may include a number of components, which are not shown in FIG. 1, such as a beam expander, folding mirrors, focusing lenses, cylindrical lenses, beam splitters, etc.

In some cases, the system may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As shown in FIG. 1, the system may be configured to direct the beam of light to the specimen at a normal angle of incidence. In this embodiment, the system may not include a deflector since the normal incidence beam of light may be scanned over the specimen by relative motion of the optics with respect to the specimen and/or by relative motion of the specimen with respect to the optics. Alternatively, the system may be configured to direct the beam of light to the specimen at an oblique angle of incidence. The system may also be configured to direct multiple beams of light to the specimen such as an oblique incidence beam of light and a normal incidence beam of light. The multiple beams of light may be directed to the specimen substantially simultaneously or sequentially.

The system includes a detection subsystem configured to generate output responsive to light scattered from the specimen. The output can be used to detect defects on the specimen. The detection subsystem may include a single collection channel. For example, light scattered from the specimen may be collected by collector 16, which may be a lens, a compound lens, or any appropriate lens known in the art. Alternatively, is collector 16 may be a reflective or partially reflective optical component, such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen. Furthermore, the detection subsystem may include more than one collection channel (not shown), each of which is configured to collect light scattered at different collection angles.

The detection subsystem also includes detector 18 for detecting the light scattered from the specimen and collected by collector 16. Detector 18 generally functions to convert the scattered light into an electrical signal, and therefore, may include substantially any photodetector known in the art. However, a particular detector may be selected for use in one or more embodiments of the system based on desired performance characteristics of the detector, the type of specimen to be inspected, and/or the configuration of the components configured to direct the light to the specimen. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes, and photomultiplier tubes (PMTs) may be used, depending on the amount of light available for inspection and the type of inspection being performed. In at least one embodiment, a PMT is used for detecting light scattered from a specimen. In addition, if the detection subsystem includes more than one collection channel as described above, the detection subsystem may include more than one detector (not shown), each of which is configured to detect the light collected by one corresponding collection channel.

The system may also include various components used for processing the output generated by the detection subsystem. For example, the system shown in FIG. 1 includes amplifier 20, analog-to-digital converter (ADC) 22, and processor 24. Amplifier 20 is generally configured to receive output from detector 18 and to amplify the output by a predetermined amount. ADC 22 converts the amplified output into a digital format suitable for use by processor 24. In one embodiment, the processor may be coupled directly to ADC 22 by a transmission medium, as shown in FIG. 1. Alternatively, the processor may receive output from other electronic components coupled to ADC 22. In this manner, the processor may be indirectly coupled to ADC 22 by a transmission medium and any intervening electronic components. If the detection subsystem includes more than one detector as described above, the output generated by each detector may be provided to the processor in a similar manner.

The processor may be configured to use the output generated by the detection subsystem to detect defects on the specimen. In addition, processor 24 may be configured for detecting features, defects, light scattering properties, or some combination thereof of the specimen using the output generated by the detection subsystem. The output is representative of the light detected by a detector (detector 18). The term "detector" as used herein generally refers to a detector having only one sensing area or possibly several sensing areas (such as found, e.g., in a detector array or multi-anode PMT). Regardless of number, the sensing areas of a detector are embodied within a single enclosure. In some cases, the system described herein may be used for inspecting patterned, as well as unpatterned specimens. The processor may include any appropriate processor known in the art. In addition, the processor may be configured to use any appropriate defect detection algorithm and/or method known in the art. For example, the processor may use a die-to-database comparison or a thresholding algorithm to detect defects on the specimen. The processor may also be configured to perform any other defect-related functions known in the art.

The system shown in FIG. 1 includes a power attenuator subsystem configured to alter a power level of light directed to the specimen during inspection between at least two power levels including a full power level and a minimum power level equal to or greater than about 10% of the full power level. In other words, the full power level may be equal to about 100% transmission of the light generated by the light source, and the minimum power level may be equal to or greater than about 10% transmission of the light generated by light source 10. As described further herein, the power attenuator subsystem is preferably configured such that the minimum power level is the minimum achievable power level of the power attenuator subsystem. In this manner, the minimum achievable power level of the power attenuator subsystem may be less than full extinction (i.e., at least greater than 0% transmission).

The minimum power level may be selected based on the power level at which onset of damage to defects, features, or other materials on the specimen occurs and the power level that allows sufficient light scattered from the specimen to be detected. In this manner, the minimum power level may be selected such that damage to the specimen may be substantially prevented while allowing inspection of substantially the entire specimen, which would not be possible if the minimum power level was full extinction. Therefore, the minimum power level may vary depending on, for example, the configuration of the light source and/or characteristic(s) of the specimen. In one such example, the minimum power level used for inspection of different specimens by the same system may be different based on the characteristic(s) of the different specimens. Furthermore, the power attenuator subsystem may be configured to alter the power level of the light directed to the specimen during inspection between at least two power levels including the full power level, the minimum power level, and one or more additional power levels (e.g., one or more power levels less than the full power level and greater than the minimum power level). The one or more additional power levels may include any such appropriate power levels.

In one such embodiment shown in FIG. 1, power attenuator subsystem 26 is arranged between light source 10 and optics 12 and is configured to alter the power level of the incident light beam during a surface inspection scan. In addition, the system may include more than one light source (not shown), each of which may be similarly or different configured, or may be configured to direct more than one incident light beam to the specimen. In such instances, a power attenuator subsystem configured to alter the power level as described herein may be positioned in the path of one or more of the light beams directed to the specimen. In other instances, a power attenuator subsystem configured to alter the power level as described herein may be positioned in the path of each of the light beams directed to the specimen. If the system includes more than one power attenuator subsystem, each of the power attenuator subsystems may be similarly configured or different configured.

Figure 2:
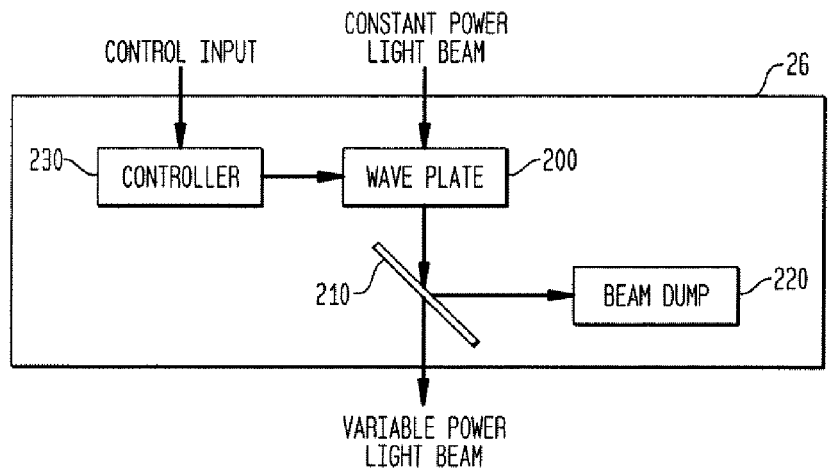
FIGS. 2-3 are block diagrams of various embodiments of a power attenuator subsystem, which may be included in the system of FIG. 1.

Power attenuator subsystem 26 may include a selectively transmissive optical component (not shown in FIG. 1), which may be configured to transmit a portion of the incident light based on a polarization of the incident light. In one embodiment, the power attenuator subsystem is configured to alter the power level by altering a position of a wave plate. For example, as shown in FIG. 2, power attenuator subsystem 26 may include wave plate 200 and polarizing beam splitter 210, in some embodiments. In this configuration, the wave plate may be used to change the polarization of the incoming light, while the beam splitter functions to transmit one or more select polarizations (e.g., linearly polarized light) and reflect all others (e.g., randomly, circularly or elliptically polarized light) to beam dump 220. By reflecting portions of the light, the wave plate and beam splitter function to reduce the intensity or power level of the light transmitted through the power attenuator subsystem. Beam dump 220 may include any appropriate component(s) known in the art.

Wave plates and similar optical components cannot be turned on and off like a switch, and instead, must be moved (e.g., rotated) in the beam path to provide two or more distinct power levels. For example, as shown in FIG. 2, power attenuator subsystem 26 may include controller 230 that is coupled to wave plate 200 and is configured to alter a position of wave plate 200 in the optical path of the constant power light beam. In particular) controller 230 may be configured to rotate wave plate 200 in the beam path. In addition, controller 230 may be configured to rotate the wave plate dynamically during inspection of the specimen such that the power level of the light directed to the specimen can be altered dynamically during inspection as described further herein. Controller 230 may include any suitable device known in the art and may be configured to alter the position of the wave plate in any manner known in the art.

In one embodiment, power attenuator subsystem 26 includes wave plate 200 having a phase retardation selected such that the minimum power level achievable by the power attenuator subsystem is equal to or greater than about 10% of the full power level. In another embodiment, the power attenuator subsystem includes a wave plate having a phase retardation other than about half-wave retardation. In some embodiments, the power attenuator subsystem includes a wave plate having a phase retardation of about wavelength/2.5 ($\lambda/2.5$) retardation. In this manner, the embodiments described herein may include a wave plate oriented such that the minimum transmission through the beam splitter is roughly equal to the minimum power level (instead of being equal to full extinction near 0% transmission). For example, if a $\lambda/2.5$ wave plate is used, the transmission through the beam splitter would have a minimum of about 10% transmission. In addition, the phase retardation of the wave plate may be selected (e.g., to be a phase retardation other than half-wave retardation and possibly other than $\lambda/2.5$ retardation) based on the selected minimum power level (i.e., based on the minimum transmission of the light from the light source through the beam splitter).

Figure 3:
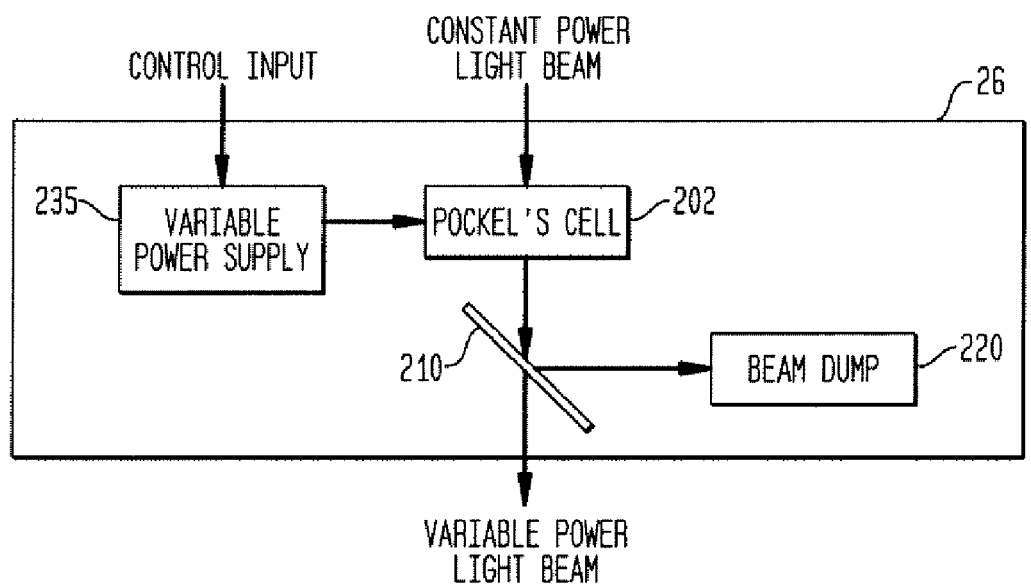

FIG. 3 illustrates another embodiment of power attenuator subsystem 26. In this embodiment, power attenuator subsystem 26 is configured to alter the power level by altering a voltage applied to Pockel's Cell 202. A Pockel's Cell may be generally defined as a high-speed electrically-controlled optical shutter. The Pockel's Cell is advantageous in that extremely fast power attenuation is provided by an electro-optical material or birefringent material of Pockel's Cell 202 that can be switched between a "full power level" condition and a "minimum power level" condition. In this manner, the electro-optical material may change the polarization of the incoming light into a predetermined polarization orientation. This so-called "re-polarized light" may then be supplied to polarizing beam splitter 210, which may transmit only a portion of the re-polarized light, depending on the particular polarization output from the electro-optical switch. If Remaining portions of the re-polarized light may be reflected by the polarizing beam splitter and absorbed by beam dump 220, which may be configured as described herein. In some cases, the electro-optical material may switch between different conditions within a time span of a few nanoseconds to a few microseconds. In this manner, faster light power attenuation can be provided by using an electro-optical switch, rather than by moving a selectively transmissive optical element in the beam path.

Initially, Pockel's Cell 202 may be set in the full power level condition to allow the light generated by light source 10 to pass freely through power attenuator subsystem 26. However, when the presence of a large particle is detected, Pockel's Cell 202 may be switched to the minimum power level condition to change the polarization of the generated light to a different polarization, which can be at least partially filtered out by polarizing beam splitter 210. To switch between the full power level and minimum power level conditions, an electrical voltage provided by variable power supply 235 may be supplied to Pockel's Cell 202 to change the polarization of the light passed through the electro-optical material (typically, an electro-optical crystal). As shown in FIG. 3, the voltage supplied to the Pockel's Cell may be determined by a control signal input to variable power supply 235. Variable power supply 235 may include any suitable component(s) known in the art.

In one example, the voltage supplied to Pockel's Cell 202 (i.e., causing the cell to switch to the minimum power level condition) may alter the characteristics of the electro-optical crystal so that it changes linearly polarized light into circularly polarized light, a phenomenon frequently referred to as a "quarter wave phase shift." If the circularly polarized light is supplied to a polarizing beam splitter, which is primarily configured for reflecting circularly polarized light, the intensity or power level of the light output from power attenuator subsystem 26 can be reduced by setting the Pockel's Cell in the minimum power level condition. On the other hand, the intensity or power level of the light output from power attenuator subsystem 26 can be maintained (or increased) by setting the Pockel's Cell in the full power level condition.

However, the intensity of the light output from power attenuator subsystem 26 is dependent on polarizing beam splitter 210, as well as the phase shift produced by Pockel's cell 202. For example, polarizing beam splitters typically discriminate between two orthogonal polarizations such as, e.g., the so-called "S" and "P" polarizations. However, other polarizations of light (such as C-polarized light) may be partially transmitted, and therefore, partially redirected (e.g. into the beam dump) by the polarizing beam splitter. If a voltage is applied such that the Pockel's cell creates a ¼ wave phase shift, incoming linearly polarized light (typical laser output) will become circularly polarized and half of that light will pass through the polarizing beam splitter, while the other half is redirected. For a ½ wave shift, no light will pass through the polarizing beam splitter except for some leakage due to imperfection of the optical components. In other words, virtually all of the incoming light will be redirected when the Pockel's Cell is configured to produce a ½ wave shift (assuming that in the power off state all light passes through the beam splitter).

In some cases, the constant power light beam generated by light source 10 can be divided into two distinct power levels (e.g., a "minimum" power level and a "full" power level) by dynamically switching an electro-optical shutter (such as a Pockel's Cell) between minimum power level and full power level conditions. The minimum power level may be substantially less than the full power level to prevent thermal damage when scanning over large particles. For example, the minimum power level may be some percentage (ranging, e.g., between about 1% and about 50%) of the full power level. In one embodiment, the minimum power level is about 10% of the full power level. In a different embodiment, the minimum power level is about 5% of the full power level. Other possibilities exist and may generally depend on the incident power, as well as the size and material composition of the particles being scanned.

In other cases, an electro-optical shutter (such as a Pockel's Cell) may be configured for generating more than two distinct power levels. For example, a Pockel's Cell can be driven to produce substantially any phase shift, and thus, may be combined with a polarizing beam splitter to create substantially any output power level. In other words, the embodiment shown in FIG. 3 can be used to create substantially any number of distinct power levels. In some cases, circuitry and/or software may be included in the system to provide a continuous power level adjustment, e.g., in the form of a closed feedback loop, as shown in FIG. 11 described further herein.

In one embodiment, power attenuator subsystem 26 includes Pockel's Cell 202 oriented such that the minimum power level achievable by the power attenuator subsystem is equal to or greater than about 10% of the full power level. In another embodiment, the power attenuator subsystem includes a Pockel's Cell oriented at an angle other than about 0 degrees or about 45 degrees from a full extinction position of the Pockel's Cell. In an additional embodiment, the power attenuator subsystem includes a Pockel's Cell oriented at an angle of about 5 degrees to about 40 degrees from a full extinction position of the Pockel's Cell. In a further embodiment, the power attenuator subsystem includes a Pockel's Cell oriented at an angle of about 18.5 degrees from a full extinction position of the Pockel's Cell. In addition, the angle at which the Pockel's Cell is oriented from a full extinction position may be selected based on the selected minimum power level (i.e., based on the minimum transmission of the light from the light source through the power attenuator subsystem). In this manner, the embodiments described herein may include a Pockel's Cell oriented such that the minimum transmission through the beam splitter is roughly equal to the minimum power level (instead of being equal to full extinction near 0% transmission). For example, if the Pockel's Cell is rotated about 18.5 degrees from nominal (i.e., the best extinction position) about the optical axis, the transmission through the power attenuator subsystem would have a minimum at about 10% transmission.

The embodiments of the power attenuator subsystem described above provide a number of advantages over other power attenuation methods and systems. One main advantage of the embodiments described herein is an improvement in the stability of the optical attenuators. For instance, in one embodiment, the power attenuator subsystem is configured such that a stability of the minimum power level is greater than a stability of a full extinction power level. In another embodiment, the power attenuator subsystem is configured such that the minimum power level is substantially insensitive to changes in alignment of the light source. In an additional embodiment, the power attenuator subsystem is configured such that the minimum power level is substantially insensitive to changes in a voltage applied to one or more elements of the power attenuator subsystem. In this manner, the systems described herein can be used for opto-mechanical adjustment of illumination (e.g., laser) power with improved power stability. In particular, the systems described herein address the power stability issues in other system configurations for power levels near extinction. In addition, the embodiments described herein that include a two or more level (or two or more "position") wave plate/beam splitter type attenuator with wave plate phase retardation described herein can be used to obtain power transmission levels with greatly improved stability for high and low power levels. Furthermore, the embodiments described herein that include a two or more level (or two or more "position") Pockel's Cell type attenuator with a Pockel's Cell alignment angle about the optical axis described herein can be used to obtain power transmission levels with greatly improved stability for the high and low power levels.

Such attenuators may also be incorporated into existing inspection systems to improve the performance, manufacturability, and reliability of the inspection systems. Moreover, the embodiments described herein can be incorporated into existing inspection systems without incurring substantial additional cost of goods (COGs) compared to other systems for altering the power level of light directed to a specimen while providing substantial improvements over those other systems.

The sensitivity of the transmission of the power attenuator subsystem to phase shift or alignment angle variations may be determined as follows. The electric field vector from the light (e.g., laser) source can be determined from the following equation:

$$\vec{e}_{Laser} = a_0 \times e^{i\omega t} \times \begin{pmatrix} 0 \\ 1 \end{pmatrix} \qquad (1)$$

Figure 4:
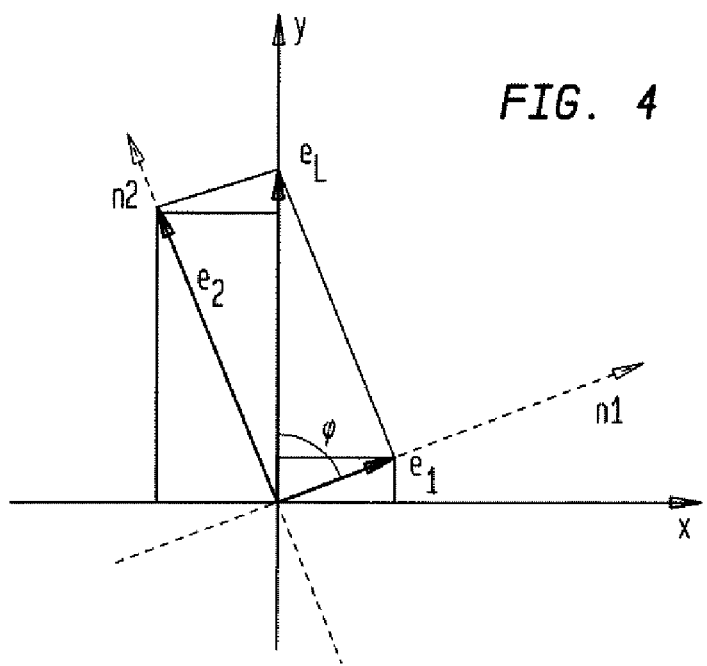
FIG. 4 is a diagram illustrating the field vector from a light source split into two vectors along the fast and slow axes of a Pockel's Cell or wave plate.

The field vector at the Pockel's Cell or wave plate entrance, with angle, $\phi$, of fast axis vs. x-axis, can be determined from the electric field vector from the light source. In particular, the field vector splits into two vectors along the fast axis and the slow axis, as shown schematically in FIG. 4 and according to the following equation;

$$\vec{e}_{Laser} = \vec{e}_1 + \vec{e}_2 \qquad (2)$$

$$= a_0 \times e^{i\omega t} \times \left( \cos\varphi \times \begin{pmatrix} \sin\varphi \\ \cos\varphi \end{pmatrix} + \sin\varphi \times \begin{pmatrix} -\cos\varphi \\ \sin\varphi \end{pmatrix} \right)$$

where $\vec{e}_1$ is the electric field vector along the fast axis, $\vec{e}_2$ is the electric field vector along the slow axis, and n1 and n2 are the refractive indices of the Pockel's Cell or wave plate along the fast and slow axes, respectively. At the Pockel's Cell or wave plate exit, a phase shift of $+/-\Delta/2$ is introduced for the fast and slow axes, respectively, as shown in the following equations:

$$\vec{e}_P = \vec{e}_1 \times e^{i\Delta/2} + \vec{e}_2 \times e^{-i\Delta/2} \qquad (3)$$

$$= a_0 \times e^{i\omega t} \times \left( e^{i\Delta/2} \times \begin{pmatrix} \sin\varphi\cos\varphi \\ \cos^2\varphi \end{pmatrix} + e^{-i\Delta/2} \times \begin{pmatrix} -\cos\varphi\sin\varphi \\ \sin^2\varphi \end{pmatrix} \right)$$

$$\vec{e}_P = a_0 \times e^{i\omega t} \times \begin{pmatrix} \sin\varphi\cos\varphi \times (e^{i\Delta/2} - e^{-i\Delta/2}) \\ \cos^2\varphi \times e^{i\Delta/2} + \sin^2\varphi \times e^{-i\Delta/2} \end{pmatrix} \qquad (4)$$

$$\vec{e}_P = a_0 \times e^{i\omega t} \times \begin{pmatrix} i\sin(\Delta/2) \times \sin 2\varphi \\ \cos(\Delta/2) \times (\cos^2\varphi + \sin^2\varphi) + \\ i\sin(\Delta/2) \times (\cos^2\varphi - \sin^2\varphi) \end{pmatrix} \qquad (5)$$

$$\vec{e}_P = a_0 \times e^{i\omega t} \times \begin{pmatrix} i\sin(\Delta/2) \times \sin 2\varphi \\ \cos(\Delta/2) + i\sin(\Delta/2) \times \cos 2\varphi \end{pmatrix} \qquad (6)$$

The light intensity after a polarizer (e.g., polarizing beam splitter 210 shown in FIGS. 2 and 3) in the x- and y-directions is the square of the absolute values of the intensities according to the following equations:

$$\vec{e}_P = a_0 \times e^{i\omega t} \times \begin{pmatrix} i\sin(\Delta/2) \times \sin 2\varphi \\ \cos(\Delta/2) + i\sin(\Delta/2) \times \cos 2\varphi \end{pmatrix} \qquad (7)$$

$$e_{P_x}^2 = a_0^2 \times \sin^2(\Delta/2) \times \sin^2 2\varphi \qquad (8)$$

$$e_{P_y}^2 = a_0^2 \times (\cos^2(\Delta/2) + \sin^2(\Delta/2) \times \cos^2 2\varphi) \qquad (9)$$

$$e_{P_y}^2 = a_0^2 \times (\cos^2(\Delta/2) + \sin^2(\Delta/2) \times (1 - 1 + \cos^2 2\varphi)) \qquad (10)$$

$$e_{P_y}^2 = a_0^2 \times (1 - \sin^2(\Delta/2) \times (\sin^2 2\varphi)) \qquad (11)$$

The transmission, t, is the ratio of incoming light to transmitted light according to the following equation:

$$t = \frac{e_{P_y}^2}{e^2 L} = 1 - \sin^2(\Delta/2) \times \sin^2 2\varphi \qquad (12)$$

The sensitivity of the transmission value to phase shift or alignment angle variation is given by the derivatives:

$$\frac{\partial t/\partial \Delta}{t} = \frac{-1/2\sin\Delta \times \sin^2 2\varphi}{1 - \sin^2(\Delta/2) \times \sin^2 2\varphi} \qquad (13)$$

$$\frac{\partial t/\partial \varphi}{t} = \frac{-2\sin^2(\Delta/2) \times \sin 4\varphi}{1 - \sin^2(\Delta/2) \times \sin^2 2\varphi}$$

Figure 5:
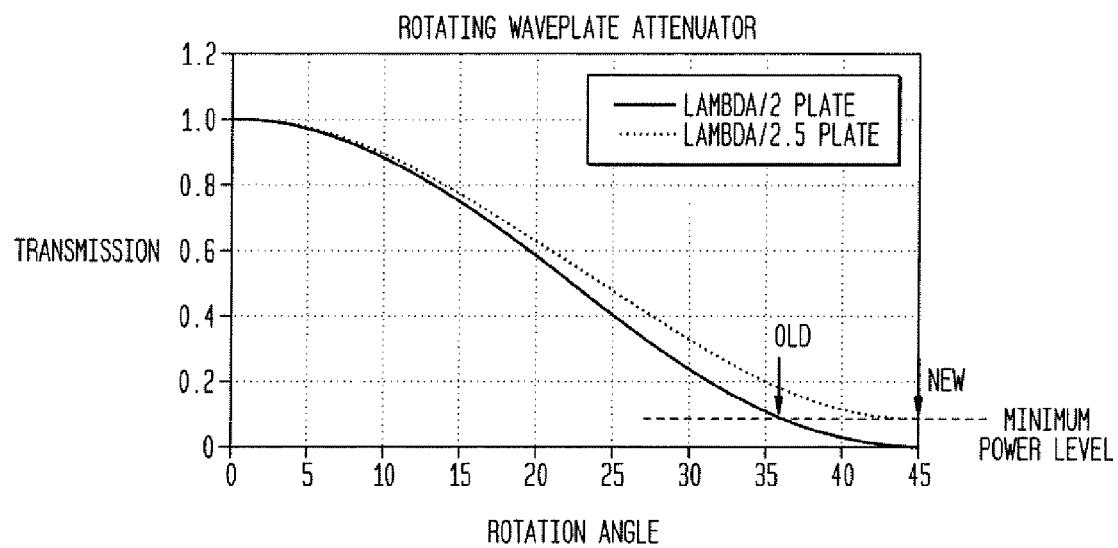
FIG. 5 is a plot illustrating power attenuation as a function of rotation angle of different wave plates.
Figure 6:
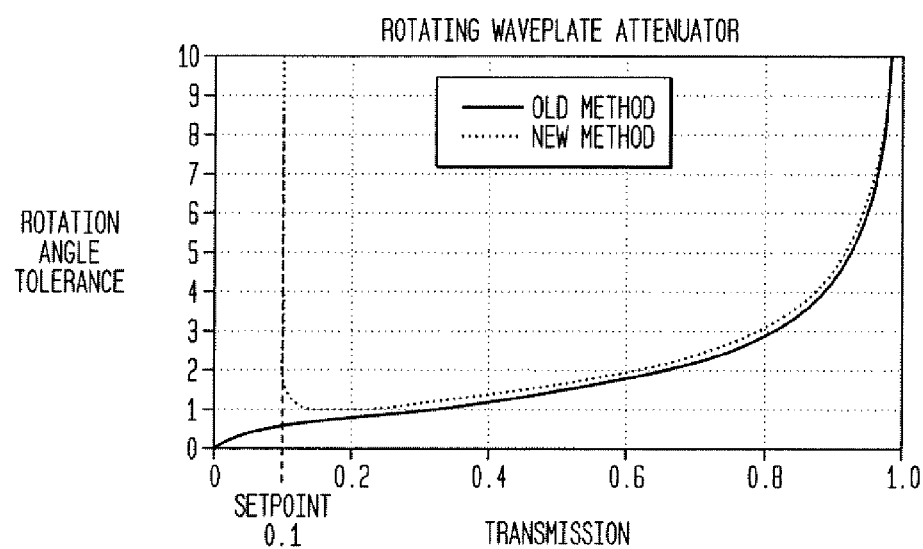
FIG. 6 is a plot illustrating allowed rotation angle tolerance of different wave plates as a function of transmission.

Unlike inspection systems that include a power attenuator having a phase shift of $\lambda/2$, the embodiments described herein may include a wave plate with variable alignment angle, $\phi$, and a phase shift of $\lambda/2.5$. In both cases, the desired transmission at the minimum power level is about 10%. FIG. 5 shows power attenuation (transmission) as a function of rotation angle for a $\lambda/2$ wave plate and a $\lambda/2.5$ wave plate. As shown in FIG. 5, for the "new" $\lambda/2.5$ wave plate, the transmission corresponding to the minimum power level falls into the relatively flat region of the curve, thus making the minimum power level much more stable with respect to phase shift variations. In contrast, for the "old" $\lambda/2$ wave plate, the transmission corresponding to the minimum power level falls into a relatively steep region of the curve making the minimum power level much less stable with respect to phase shift variations. FIG. 6 shows the allowed rotation angle tolerance to maintain transmission to 10% accuracy. Near the minimum power level, the "old method" $\lambda/2$ wave plate transmission is significantly more sensitive to alignment angle variation (less than about 0.5 degrees) than the "new method" $\lambda/2.5$ wave plate. In other words, the rotation angle tolerance of the $\lambda/2.5$ wave plate at a transmission of about 10% is significantly higher than the rotation angle tolerance of the $\lambda/2$ wave plate at a transmission of about 10%. Therefore, the minimum power level of a power attenuator subsystem that includes a $\lambda/2.5$ wave plate will be more stable than the minimum power level of a power attenuator subsystem that includes a $\lambda/2$ wave plate. In addition, the power attenuator subsystem described herein may be configured such that the minimum power level is substantially insensitive to changes in alignment of the light source due to the significantly higher rotation angle tolerance of the power attenuator subsystem.

Figure 7:
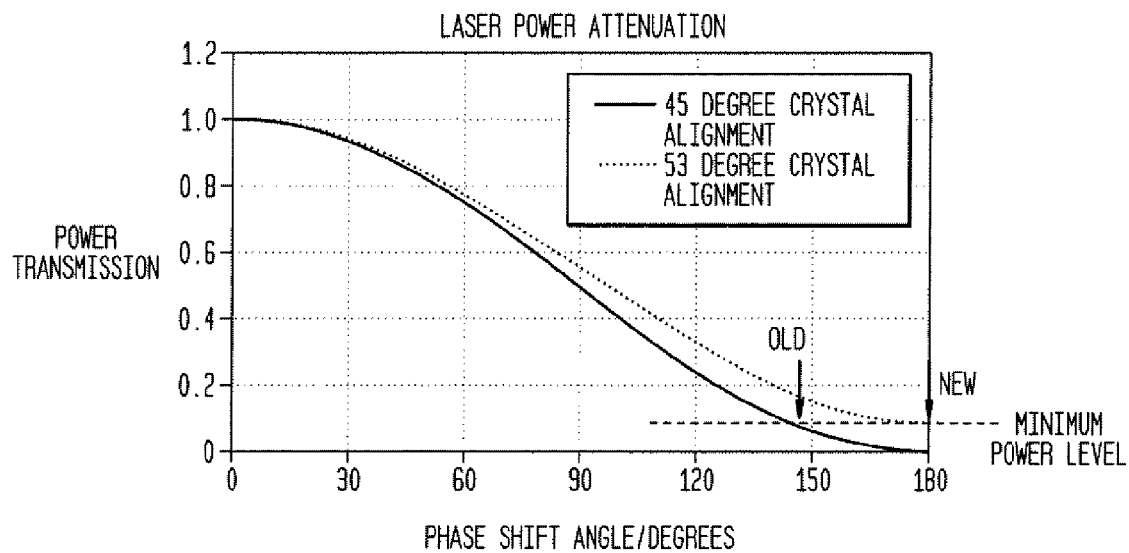
FIG. 7 is a plot illustrating power attenuation as a function of phase shift for different Pockel's Cell alignment angles.
Figure 8:
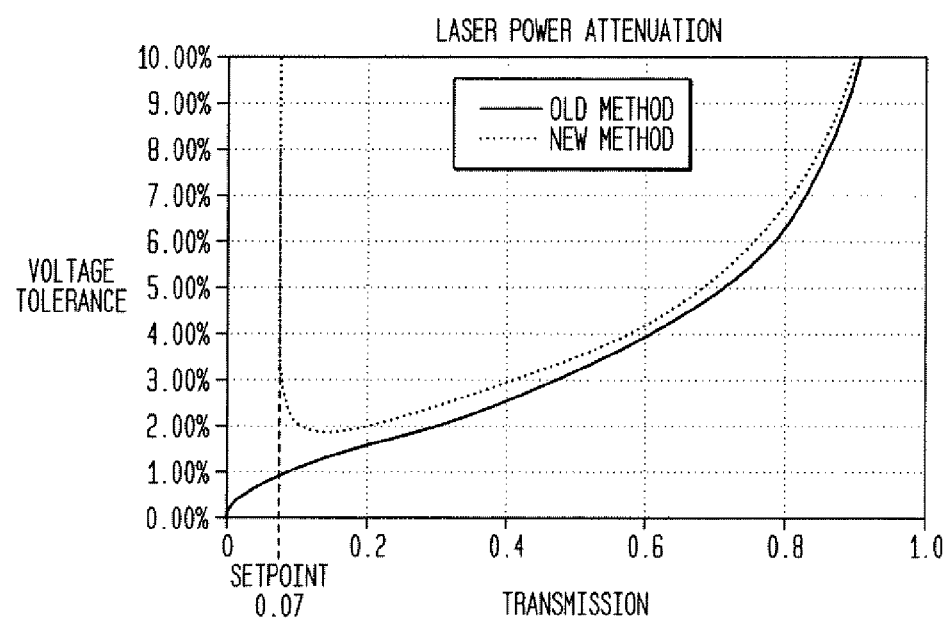
FIG. 8 is a plot illustrating Pockel's Cell phase shift tolerance for different alignment angles of the Pockel's Cell as a function of transmission.

As described above, the power attenuator subsystem may include a Pockel's Cell at an alignment angle, $\phi$, with variable phase shift, $\Delta$. FIG. 7 illustrates power attenuation (power transmission) as a function of phase shift for Pockel's Cell alignment angles of 45 degrees and 53 degrees. As shown in FIG. 7, for the "old" 45 degree alignment angle, the transmission ratio of 0.07 corresponding to the minimum power level falls into a relatively steep portion of the transmission vs. phase shift curve. However, for the "new" 53 degree angle, the transmission corresponding to the minimum power level falls into the relatively flat region of the curve, thus making the minimum power level much more stable with respect to phase shift variations. FIG. 8 illustrates the Pockel's Cell phase shift (voltage, HV) tolerance as a function of transmission. As shown in FIG. 8, near a minimum power level of 0.07, the "old method" 45 degree alignment angle requires about 1% voltage stability to maintain the transmission within 10% accuracy, while the 53 degree alignment angle provides an error margin of greater than about 5%. Therefore, a stability of the minimum power level of the power attenuator subsystem embodiments described herein may be greater than a stability of a full extinction power level. In addition, the power attenuator subsystems described herein may be configured such that the minimum power level is substantially insensitive to changes in a voltage applied to one or more elements (e.g., the Pockel's Cell) of the power attenuator subsystem.

In addition to the various means described above for dynamically altering a power level of a light beam, the system of FIG. 1 provides means for controlling such alteration. For example, power controller subsystem 28 may be coupled between one or more elements of the detection subsystem (e.g., collector 16, photodetector 18, amplifier 20, ADC 22 and processor 24) and power attenuator subsystem 26. As described in more detail below, power controller subsystem 28 may continuously monitor the light scattered from specimen 14 and detected by the detection subsystem to determine whether the detected scattered light is above or below a predetermined threshold level. Based on such determination, power controller subsystem 28 may instruct power attenuator subsystem 26 to provide the incident light to the specimen at either a first power level (e.g., a "full" power level) or a second power level (e.g., a "minimum" power level). The power controller subsystem may also cause the power attenuator subsystem to provide, e.g., a third, fourth, fifth, etc. power level to the specimen, if more than two power levels are available and circumstances warrant (or benefit from) such levels.

In general, the predetermined threshold level may be selected to reduce or prevent thermal damage that may be caused when incident light directed to the specimen is absorbed and inadequately dissipated by a feature on the specimen. The predetermined threshold level is typically based on the incident power density, and more specifically, on a power density associated with the onset of thermal damage inflicted on a feature or particle of certain size. For example, the predetermined threshold level may be selected from a group of incident power densities ranging from about 1 kW/cm$^2$ to about 1000 kW/cm$^2$ to avoid damaging relatively large particles (e.g., greater than about 5 µm), When scanning organic materials, the predetermined threshold level may range from about 1 kW/cm$^2$ to about 100 kW/cm$^2$ to avoid damaging large particles with relatively poor heat dissipation. As shown in FIG. 1, the predetermined threshold level may be supplied from processor (or computer system) 24 to power controller subsystem 28. The predetermined threshold level may be selected manually by a user of the system or automatically by processor 24.

If the detected scattered light is below the predetermined threshold level, power controller subsystem 28 may instruct power attenuator subsystem 26 to maintain the power of the incident beam at the "full" power level. However, power controller subsystem 28 may provide instructions to reduce the power of the incident beam to a "safe" or "minimum" power level, if the detected scattered light exceeds the predetermined threshold level (indicating, e.g., that a large particle is near). Once the incident beam scans over the large particle (or other highly scattering feature), the detected scattered light may fall below the predetermined threshold level, causing power controller subsystem 28 to instruct the power attenuator subsystem to increase the incident beam back to "full" power.

In this manner, the inspection system described herein may be uniquely configured for detecting features of relatively small size by directing the incident light to the specimen at a first power level (e.g., "full" power), while features of relatively larger size may be detected by directing the incident light to the specimen at a second power level (e.g., "safe" or "minimum" power). In addition, the larger features may be detected, without inflicting thermal damage on those features, by setting the second power level substantially lower than the first. If more than two power levels are available, power controller subsystem 28 may compare the detected scattered light against two or more threshold levels, and instruct the power attenuator subsystem to maintain, reduce, or increase the incident light to an appropriate power level based on such comparison.

FIG. 9 illustrates one embodiment of a preferred power controller subsystem 28. In the embodiment shown, power controller subsystem 28 includes divider 240 for normalizing the detector output against the incident power and detector gain. As such, divider 240 may be used to calculate the normalized scatter power, and thus, may be alternatively referred to as a scatter power calculator. In one example, the scatter power may be computed by dividing the detector output by the incident power and detector gain, or:

$$ScatterPower = \frac{DetectorOutput}{(LaserPower)(DetectorGain)} \qquad (14)$$

By normalizing the detector output in such a manner, the power controller subsystem causes the power attenuator subsystem to consistently switch at the same scatter light level, rather than switching at a given signal level. In other words, all signals become larger when the detector gain is increased. If the detector output is not normalized when the detector gain is increased, switching could occur at a smaller particle size than actually intended. Normalizing the detector output against incident power and detector gain enables one to consistently switch (e.g., to a lower power level) once a particle of a given size is detected.

As shown in FIG. 1, power controller subsystem 28, and therefore divider 240, may receive the detector output (i.e., the scattered light detected from the specimen) as an analog signal from photodetector 18, or alternatively, as a filtered and digitized signal from ADC 22 or processor 24. The detector gain (i.e., the current amplification associated with the detector) is supplied to divider 240 by processor 24, and may be variable or fixed depending on the particular photodetector used. As described in more detail below, however, the incident power may be supplied to divider 240 in one of two ways.

In some embodiments, the normalized scatter power signal generated by divider 240 may be fed back to processor 24, as shown by the dotted lines in FIGS. 1 and 9-11. In other words, divider 240 may be used to present the scatter data (i.e., the detector output) as a scan result, which has been normalized against incident power and detector gain. By normalizing the data before it is sent to the processor, the actual defect scatter power can be used to accurately determine the size of a defect. For example, if the incident power is lowered when scanning over a large particle, the ADC counts (i.e., the detector output) will necessarily be lower than in the unauenuated case (e.g., the full power case). This means that the scan results supplied to the processor will show a smaller defect than what is actually there. Normalizing the scatter data enables the processor to more accurately determine the size of the defect.

As shown in FIG. 1, in some embodiments, an additional optional normalizer/divider 23 may be used in the data collection path between ADC 22 and processor 24 for normalizing the scatter power signal against changes in incident power. The additional divider 23 may be used along with, or as an alternative to, the normalizer/divider (240) included within power controller subsystem 28. For example, if two dividers are used, divider 23 may be placed in the data collection path for normalizing the scatter power signal sent to processor 24, while divider 240 is placed in the threshold path for normalizing the scatter power signal sent to another power controller subsystem component (e.g., comparator 250, as discussed below). However, there may exist other options in which: only one divider is used (either in the data collection path or the threshold path), or no dividers are used (in which case, the system would not support dynamic range extension, as discussed below).

As noted above, the incident power may be supplied to divider 240 in one of two ways. In the embodiment of FIG. 9, the actual power of the incident beam is measured by power detector subsystem 27, which may be arranged in the beam path below power attenuator subsystem 26. In this embodiment, power detector subsystem 27 is configured to monitor the actual intensity or power level output from power attenuator subsystem 26. The power measured by the power detector subsystem (i.e., the Measured Power) is supplied to power controller subsystem 28 for calculating the normalized scatter power. The power detector subsystem may be implemented with substantially any power detecting means including, but not limited to, a photodiode and a PMT, among others. As described in more detail below, however, power detector subsystem 27 may not be included in all embodiments described herein.

As shown in FIG. 9, power controller subsystem 28 may also include comparator 250 for comparing the normalized scatter power to one or more predetermined threshold levels supplied by processor 24. As noted above, the threshold level(s) may be selected by a user or processor of the system to effectively reduce thermal damage when scanning over large (or other highly scattering) particles. In one embodiment, comparator 250 may receive only one threshold level (referred to as a "safe scatter threshold"), which indicates a power density associated with a maximum amount of "safe" scatter power. After comparing the normalized scatter power to the safe scatter threshold, comparator 250 may instruct power attenuator subsystem 26 to maintain, reduce, or increase the incident beam to an appropriate power level (e.g., a "full" or "safe" power level) by maintaining or changing the Power Mode supplied to the attenuator subsystem. In general, the Power Mode may be any control signal that causes the attenuator subsystem to maintain or change the output power level. In the embodiment of FIG. 3, for example, the Power Mode supplied to the attenuator subsystem may be functionally equivalent to the control signal input to variable power supply 235.

FIG. 10 illustrates another embodiment of a preferred power controller subsystem 28. In particular, FIG. 10 illustrates one manner in which the normalized scatter power can be calculated if a power detector subsystem is not used to provide a measurement of the actual power level output from power attenuator subsystem 26. Instead of receiving the Measured Power, divider 240 may be coupled to the output of comparator 250 for receiving the Power Mode control signal supplied to the attenuator subsystem. Based on the control signal, divider 240 may determine the appropriate incident power to be used in the scatter power calculations by means of, e.g., a look up table. In the embodiments is shown in FIGS. 9 and 10, divider 240 and comparator 250 may be implemented with hardware, software or a combination of both. In one example, divider 240 may be implemented in software, whereas comparator 250 may be implemented in hardware.

FIG. 11 illustrates yet another embodiment of a preferred power controller subsystem 28. In particular, FIG. 11 illustrates one manner in which continuous power adjustment may be provided by power controller subsystem 28. Like the previous embodiment, divider 240 may be coupled for receiving the detector gain and output, and for generating a normalized scatter power signal in response thereto. However, instead of supplying the normalized scatter power signal to a comparator (as shown in FIGS. 9-10), the scatter power signal is supplied to control loop feedback filter 260, which dynamically adjusts the output Power Mode based on the supplied signal. In FIG. 11, the scatter power signal is used in the feedback loop to adjust the incident power, e.g. to achieve a constant detector output signal. Therefore, instead of fixed power levels, the embodiment shown in FIG. 11 provides a continuously adjustable power level.

Any of the embodiments of the power attenuator subsystem described herein may be configured to alter the power level dynamically based on the output generated by the detection subsystem. In one embodiment, the minimum power level is below an incident power density associated with onset of thermal damage of a feature of predetermined size (e.g., greater than about 5 μm) on the specimen. In one such embodiment, the minimum power level is above an incident power density associated with a minimum of the scattered light that must be detected by the detection subsystem to generate the output that can be used to detect defects on the specimen. In this manner, substantially the entire specimen may be inspected without causing thermal damage. In a further embodiment, the power attenuator subsystem is configured to alter the power level to the full power level during the inspection of features smaller than a predetermined size (e.g., less than about 5 μm) on the specimen.

In this manner, the circuits and systems described herein may reduce thermal damage to large particles (e.g., greater than about 5 μm) by dynamically adjusting the intensity or power level of the incident beam during a surface inspection scan. In one example, thermal damage may be reduced by as much as 100% over fixed incident beam inspection systems. The circuits and systems described herein may be tailored to a variety of scan operations by providing one or more predetermined threshold levels, which may be used for dynamically switching between two or more incident beam power levels during the scan operation. In this manner, thermal damage may be reduced, or even avoided, by reducing the incident power to a lower power level (e.g., a "safe" power level) when scanning over large, highly scattering particles. However, detection sensitivity is maintained by scanning lower-scatter regions at a higher power level (e.g., "full" power level), which allows the system to detect smaller defects.

In alternative embodiments, an adaptive learning process may be used for altering the threshold levels and/or power levels based on previous or current inspection scan results. As one advantage, an adaptive learning process would allow a longer delay time for the switching electronics, because the decision would be made far in advance of the actual switching event, rather than "on the fly" just before switching is needed. Though accuracy may be increased, such an embodiment would obviously increase the complexity (and probably the cost) of the circuits and systems described above. As a mid-range alternative, a scaled relationship between scatter power and incident power levels may be established, in some embodiments, for continuously altering the amount of incident power supplied to the specimen. This alternative could be used to provide a scatter light signal that is always near the optimal range for the PMT, due to the continual adjustment of the incident power supplied to the specimen.

Though the use of a single photodetector may be preferred in some embodiments, an additional detector may be included in the system for selecting an appropriate power level for the light directed to the specimen. If included, the separate detector may be used to monitor the light scattered from the specimen. However, unlike the original detector, which is used for detecting the scattered light so that the incident power level may be adjusted accordingly, the additional detector may be used for selecting a particular threshold level or "switch point", which may then be used for selecting an appropriate power level of the light to be directed to the specimen.

In addition to reducing thermal damage, the circuits and systems described herein may also be used to increase the measurement detection range of an inspection system. Usually, the detection range of a fixed-power inspection system is limited to the detection range of the photodetector. However, by providing a variable-power inspection system, the embodiments described herein significantly increase the measurement detection range by approximately:

$$(\text{Photodetector detection range}) \times (\text{Attenuator detection range}) \qquad (15)$$

In some cases, the additional detection range provided by the power attenuator subsystem may increase the overall measurement detection range of the system by about 2 times to about 16 times. When combined with other circuit(s), system(s), method(s), or some combination thereof described in commonly assigned, copending U.S. patent application Ser. No. 11/181,228 filed Jul. 14, 2005 by Wolters et al., Ser. No. 11/181,237 filed Jul. 14, 2005 by Wolters et al., and Ser. No. 11/81,519 filed Jul. 14, 2005 by Wolters et al., which are incorporated by reference as described herein, (such as the improved PMT detector and/or dual-output amplifier), the overall measurement detection range of the inspection system may be improved by about 2 times to about 10,000 times over conventional techniques. The embodiments described herein may also be further configured as described in these patent applications. The embodiments described herein may also include any of the step(s) of any of the method(s) described in these patent applications.

FIG. 1 also illustrates an embodiment of a system configured to provide illumination of specimen 14 for inspection. The system includes power attenuator subsystem 26 that is configured to alter a power level of light directed to the specimen during the inspection between at least two power levels including a full power level and a minimum power level equal to or greater than about 10% of the full power level. The power attenuator subsystem may be further configured as described herein. In addition, the system may be further configured as described herein. Furthermore, this system has all of the advantages of other embodiments described herein.

Another embodiment relates to a method for inspecting a specimen. The method includes altering a power level of light directed to the specimen during inspection between at least two power levels including a full power level and a minimum power level equal to or greater than about 10% of the full power level. Altering the power level may be performed as described herein. The method also includes generating output responsive to light scattered from the specimen. The output can be used to detect defects on the specimen. The output may be generated as described herein. In addition, the output may be used to detect defects on the specimen as described herein. The method may be performed by any of the system embodiments described herein. In addition, the method may include any other step(s) described herein. The method also has all of the advantages of other embodiments described herein.

FIG. 12 is a flow chart diagram illustrating an exemplary method for inspecting a specimen with a variable power inspection system, such as described above. Various method steps set forth in FIG. 12 may be performed by components included within the inspection system, although certain steps may be performed by a user of the inspection system.

In some embodiments, the method begins by directing light to a specimen at a first power level (in step 300). For example, an incident beam may be directed to the specimen at a relatively high power level (such as a "full" power level) so that relatively small features or defects can be detected. As described in more detail below, the incident beam may be subsequently reduced to a lower power level (such as a "safe" power level) so that relatively large features or defects can be detected without damaging those features or defects. The method shown in FIG. 12 can be modified for dynamically switching between more than two power levels, as desired.

In most cases, the method may detect light scattered from the specimen (in step 304) while scanning the light over a surface of the specimen (in step 302). For example, scattered light may be detected from the specimen when an incident beam is directed to a current location on the specimen. The scattered light detected at the current location may be used (in step 306) for detecting features, defects, or light scattering properties of the specimen at that location. The beam position may then be scanned to a nearby location, where the process is repeated for detecting features, defects, or light scattering properties at the nearby location.

In some embodiments, scanning may be implemented by placing an optical deflector in the path of the beam directed to the specimen. For example, the deflector may be included within beam forming and polarization control optics 12 of FIG. 1. In some embodiments, the deflector may include an acousto-optical deflector (AOD), a mechanical scanning assembly, an electronic scanner, a rotating mirror, a polygon based scanner, a resonant scanner, a piezoelectric scanner, a galvo mirror, or a galvanometer. In some embodiments, the deflector may scan the light beam over the specimen at an approximately constant scanning speed. For example, the light beam may be scanned over the specimen at a substantially constant scanning speed selected from a range of speeds between about 0 m/s and about 24 m/s. In other embodiments, the deflector may scan the light beam over the specimen at a variable scanning speed ranging between about 0 m/s to about 24 m/s. However, a deflector may not be needed to implement scanning in all embodiments of the invention. For example, a normal incidence beam of light may be scanned over the specimen by relative motion of the beam forming optics with respect to the specimen, and/or by relative motion of the specimen with respect to the optics.

During the scanning process, the method monitors light scattered from the specimen at a nearby location (in step 308), while light scattered from the specimen is detected at the current location (in step 304). For example, an incident beam may be supplied to the specimen with a power density distribution that peaks near the middle of the distribution and tapers off near the edges of the distribution. As used herein, the middle of the distribution will be referred to as the "main beam," while the edges are referred to as the "beam skirt." One example would be a power density distribution with a main lobe and at least one side lobe on each side of the main lobe; the side lobes having a smaller power density, and therefore, a smaller amplitude than the main lobe. Another example is a bell-shaped or Gaussian distribution whose one main lobe has a gradually tapered beam skirt.

When scanning over the surface of the specimen, the beam skirt of the incident beam may reach a particle or defect (e.g., on the order of one to several microseconds) before the particle or defect is reached by the main beam. For example, most particles or defects on the surface of a specimen will be significantly smaller than the spot size of the beam. This enables the beam skirt to reach a particle or defect before it is reached by the main beam. As the incident beam is scanned over the surface of the specimen, the amount of light scattered from the specimen (i.e., the scatter power) will change depending on what part of the beam is covering the particle or defect. Assume, for example, that the high power density main beam covers a relatively smooth surface of the specimen when the low power density beam skirt reaches a large particle or defect. Because the amount of light scattered from relatively smooth surfaces is typically substantially smaller than the scatter attributed to large particles or defects, the amount of scatter power attributed to the main beam portion may be considered negligible. As such, a significant increase in the scatter power may indicate that the beam skirt has reached a large particle or defect. In other words, the presence of large particles or defects may be detected at a nearby location by monitoring the scatter levels from the low power density beam skirt.

If the scatter levels from the beam skirt are substantially greater than or equal to the safe scatter threshold (in step 310), the incident beam may be reduced to a second power level, lower than the first (in step 314). As noted above, the second power level (referred to as the "safe" power level) may typically range between about 1% to about 50% of the first power level (referred to as the "full" power level), and in a preferred embodiment, may be about 10% of the full power level. If the scatter levels from the beam skirt are less than the safe scatter threshold (in step 310), the first power level will be maintained to enable smaller features to be detected and to preserve detection sensitivity.

In some cases, the method may end (in step 318), if the surface inspection scan is complete (in step 316). Otherwise, the scanning process may continue (in step 320) so that the nearby location becomes the current location. The method continues to monitor the beam skirt scatter levels while the incident beam moves over the defect. When the scatter levels fall back below the safe scatter threshold (in step 310), indicating that the high density center of the beam (i.e., the main beam) has passed the defect, the first power level will be restored (in step 312) to continue inspecting the specimen for small defects.

By using a fast power attenuator, such as those described above and shown in FIGS. 1-3, the systems and methods described herein may easily switch between high and low power levels before the main beam reaches the nearby location. For example, beam skirt scatter levels may be used to indicate the presence of a large defect at a nearby location several microseconds before the main beam reaches that location. Due in part to the relatively fast response (e.g., on the order of a few nanoseconds to a few microseconds) of power attenuator subsystem 26, the embodiments are able to reduce the incident beam power level before the main beam reaches the defect by monitoring the beam skirt scatter levels. By dynamically decreasing the power level while scanning large particles, and increasing the power level once the particle is scanned, the embodiments described herein reduce thermal damage to large particles, while maintaining system throughput and sensitivity.

Further modifications and alternative embodiments of various aspects of the invention may be apparent to those skilled in the art in view of this description. For example, systems and methods for inspecting a specimen with light at varying power levels are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a specimen, comprising:
a light source configured to generate light;
a power attenuator subsystem configured to alter a power level of the light directed to the specimen during inspection between at least two power levels comprising a full power level and a minimum power level equal to or greater than about 10% of the full power level, wherein the power attenuator subsystem comprises a Pockel's Cell oriented at an angle other than about 0 degrees or about 45 degrees from a full extinction position of the Pockel's Cell; and
a detection subsystem configured to generate output responsive to light scattered from the specimen, wherein the output is used to detect defects on the specimen.

2. The system of claim 1, wherein the power attenuator subsystem is further configured such that a stability of the minimum power level is greater than a stability of a full extinction power level.

3. The system of claim 1, wherein the power attenuator subsystem is further configured such that the minimum power level is substantially insensitive to changes in alignment of the light source.

4. The system of claim 1, wherein the power attenuator subsystem is further configured such that the minimum power level is substantially insensitive to changes in a voltage applied to one or more elements of the power attenuator subsystem.

5. The system of claim 1; wherein the power attenuator subsystem is further configured to alter the power level by altering a voltage applied to the Pockel's Cell.

6. The system of claim 1, wherein the Pockel's Cell is oriented such that the minimum power level achievable by the power attenuator subsystem is equal to or greater than about 10% of the full power level.

7. The system of claim 1, wherein the Pockel's Cell is oriented at an angle of about 5 degrees to about 40 degrees from the full extinction position of the Pockel's Cell.

8. The system of claim 1, wherein the Pockel's Cell is oriented at an angle of about 18.5 degrees from the full extinction position of the Pockel's Cell.

9. The system of claim 1, wherein the power attenuator subsystem is further configured to alter the power level dynamically based on the output.

10. The system of claim 1, wherein the minimum power level is below an incident power density associated with onset of thermal damage of a feature of predetermined size on the specimen.

11. The system of claim 1, wherein the minimum power level is below an incident power density associated with onset of thermal damage of a feature of predetermined size on the specimen and above an incident power density associated with a minimum of the scattered light that must be detected by the detection subsystem to generate the output that is used to detect defects on the specimen.

12. The system of claim 1, wherein the power attenuator subsystem is further configured to alter the power level to the full power level during the inspection of features smaller than a predetermined size on the specimen.

13. The system of claim 1, wherein the light source has an output power density of about 1 kW/cm$^2$ to about 1000 kW/cm$^2$.

14. A system configured to provide illumination of a specimen for inspection, comprising a power attenuator subsystem configured to alter a power level of light directed to the specimen during the inspection between at least two power levels comprising a full power level and a minimum power level equal to or greater than about 10% of the full power level, wherein the power attenuator subsystem comprises a Pockel's Cell oriented at an angle other than about 0 degrees or about 45 degrees from a full extinction position of the Pockel's Cell.

15. A method for inspecting a specimen, comprising:
altering a power level of light directed to the specimen during inspection between at least two power levels comprising a full power level and a minimum power level equal to or greater than about 10% of the full power level using a power attenuator subsystem, wherein the power attenuator subsystem comprises a Pockel's Cell oriented at an angle other than about 0 degrees or about 45 degrees from a full extinction position of the Pockel's Cell; and
generating output responsive to light scattered from the specimen, wherein the output is used to detect defects on the specimen.

* * * * *